United States Patent
Matsubara et al.

(10) Patent No.: US 11,234,649 B2
(45) Date of Patent: Feb. 1, 2022

(54) SYSTEMS AND METHODS FOR EVALUATING HEMODIALYSIS ARTERIOVENOUS FISTULA MATURATION

(71) Applicant: VOLCANO CORPORATION, San Diego, CA (US)

(72) Inventors: Bradley S. Matsubara, Escondido, CA (US); John Unser, Temecula, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 371 days.

(21) Appl. No.: 16/293,496

(22) Filed: Mar. 5, 2019

(65) Prior Publication Data

US 2019/0261924 A1    Aug. 29, 2019

Related U.S. Application Data

(63) Continuation of application No. 14/596,576, filed on Jan. 14, 2015, now Pat. No. 10,251,606.
(Continued)

(51) Int. Cl.
    *A61B 8/00* (2006.01)
    *A61B 5/00* (2006.01)
    (Continued)

(52) U.S. Cl.
    CPC .......... *A61B 5/6851* (2013.01); *A61B 5/026* (2013.01); *A61B 5/0215* (2013.01);
    (Continued)

(58) Field of Classification Search
    CPC .............. A61M 25/09; A61M 1/3655; A61M 2025/09083; A61M 2025/09116;
    (Continued)

(56) References Cited

U.S. PATENT DOCUMENTS

| 4,794,931 A | 1/1989 | Yock |
| 4,841,977 A | 6/1989 | Griffith et al. |

(Continued)

FOREIGN PATENT DOCUMENTS

| CA | 2 616 760 A1 | 2/2007 |
| CN | 101534718 A | 9/2009 |

(Continued)

OTHER PUBLICATIONS

Anonymous, 2006, Clinical Practice Guidelines and Clinical Practice Recommendations 2006 Updates, National Kidney Foundation:10PP.

(Continued)

*Primary Examiner* — Joel Lamprecht

(57) ABSTRACT

The invention relates to evaluation of maturity of arteriovenous (AV) fistula using guidewires that measure intravascular blood flow and/or pressure. The invention provides methods of evaluating AV fistula maturation using an instrumented guidewire to measure intravascular flow and/or pressure. By using a small diameter guidewire that does not interfere substantially with the flow, an accurate measurement can be made that is useful for identifying when a fistula is mature and therefore ready to be used for hemodialysis. The flow of blood through the fistula is measured using the guidewire and the measured flow and/or pressure of blood is used to determine if the fistula is mature.

20 Claims, 6 Drawing Sheets

Related U.S. Application Data

(60) Provisional application No. 61/927,016, filed on Jan. 14, 2014.

(51) Int. Cl.
  *A61B 8/06* (2006.01)
  *A61B 8/08* (2006.01)
  *A61B 8/12* (2006.01)
  *A61B 5/0215* (2006.01)
  *A61B 5/0265* (2006.01)
  *A61M 1/36* (2006.01)
  *A61B 5/026* (2006.01)
  *A61M 25/09* (2006.01)

(52) U.S. Cl.
  CPC ........ *A61B 5/0265* (2013.01); *A61B 5/02158* (2013.01); *A61B 8/06* (2013.01); *A61B 8/0891* (2013.01); *A61B 8/12* (2013.01); *A61B 8/445* (2013.01); *A61B 8/488* (2013.01); *A61M 1/3655* (2013.01); *A61M 25/09* (2013.01); *A61B 2560/0475* (2013.01); *A61B 2562/0247* (2013.01); *A61M 2025/0915* (2013.01); *A61M 2025/09083* (2013.01); *A61M 2025/09116* (2013.01); *A61M 2025/09175* (2013.01); *A61M 2025/09183* (2013.01)

(58) Field of Classification Search
  CPC ........... A61M 2025/09183; A61M 2025/0915; A61M 2025/09175; A61B 5/6851; A61B 8/445; A61B 5/0215; A61B 5/026; A61B 8/06; A61B 8/0891; A61B 8/12; A61B 8/488; A61B 5/02158; A61B 5/0265; A61B 2560/0475; A61B 2562/0247
  See application file for complete search history.

(56) References Cited

U.S. PATENT DOCUMENTS

| | | |
|---|---|---|
| 4,917,097 A | 4/1990 | Proudian et al. |
| 4,951,677 A | 8/1990 | Crowley et al. |
| 5,000,185 A | 3/1991 | Yock |
| 5,095,911 A | 3/1992 | Pomeranz |
| 5,125,137 A | 6/1992 | Corl et al. |
| 5,135,486 A | 8/1992 | Eberle et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,178,159 A | 1/1993 | Christian |
| 5,183,048 A | 2/1993 | Eberle |
| 5,226,421 A | 7/1993 | Frisbie et al. |
| 5,240,003 A | 8/1993 | Lancee et al. |
| 5,240,437 A | 8/1993 | Christian |
| 5,243,988 A | 9/1993 | Sieben et al. |
| 5,313,949 A | 5/1994 | Yock |
| 5,321,501 A | 6/1994 | Swanson et al. |
| 5,328,342 A | 7/1994 | Pflueger et al. |
| 5,348,017 A | 9/1994 | Thornton et al. |
| 5,353,798 A | 10/1994 | Sieben |
| 5,368,037 A | 11/1994 | Eberle et al. |
| 5,372,138 A | 12/1994 | Crowley et al. |
| 5,373,845 A | 12/1994 | Gardineer et al. |
| 5,373,849 A | 12/1994 | Maroney et al. |
| 5,375,602 A | 12/1994 | Lancee et al. |
| 5,453,575 A | 9/1995 | O'Donnell et al. |
| 5,771,895 A | 6/1998 | Slager |
| 5,830,222 A | 11/1998 | Makower |
| 5,873,835 A | 2/1999 | Hastings et al. |
| 6,068,638 A | 5/2000 | Makower |
| 6,106,476 A | 8/2000 | Corl et al. |
| 6,134,003 A | 10/2000 | Tearney et al. |
| 6,159,225 A | 12/2000 | Makower |
| 6,190,353 B1 | 2/2001 | Makower et al. |
| 6,200,268 B1 | 3/2001 | Vince et al. |
| 6,210,339 B1 | 4/2001 | Kiepen et al. |
| 6,283,951 B1 | 9/2001 | Flaherty et al. |
| 6,375,615 B1 | 4/2002 | Flaherty et al. |
| 6,381,350 B1 | 4/2002 | Klingensmith et al. |
| 6,421,164 B2 | 7/2002 | Tearney et al. |
| 6,457,365 B1 | 10/2002 | Stephens et al. |
| 6,508,824 B1 | 1/2003 | Flaherty et al. |
| 6,544,230 B1 | 4/2003 | Flaherty et al. |
| 6,551,250 B2 | 4/2003 | Khalil |
| 6,579,311 B1 | 6/2003 | Makower |
| 6,602,241 B2 | 8/2003 | Makower et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,709,444 B1 | 3/2004 | Makower |
| 6,726,677 B1 | 4/2004 | Flaherty et al. |
| 6,746,464 B1 | 6/2004 | Makower |
| 6,780,157 B2 | 8/2004 | Stephens et al. |
| 7,074,188 B2 | 7/2006 | Nair et al. |
| 7,175,597 B2 | 2/2007 | Vince et al. |
| 7,215,802 B2 | 5/2007 | Klingensmith et al. |
| 7,245,789 B2 | 7/2007 | Bates et al. |
| 7,359,554 B2 | 4/2008 | Klingensmith et al. |
| 7,387,636 B2 | 6/2008 | Cohn et al. |
| 7,447,388 B2 | 11/2008 | Bates et al. |
| 7,463,759 B2 | 12/2008 | Klingensmith et al. |
| 7,527,594 B2 | 5/2009 | Vardi et al. |
| 7,660,492 B2 | 2/2010 | Bates et al. |
| 7,736,317 B2 | 6/2010 | Stephens et al. |
| 7,783,337 B2 | 8/2010 | Feldman et al. |
| 7,787,127 B2 | 8/2010 | Galle et al. |
| 7,995,210 B2 | 8/2011 | Tearney et al. |
| 7,999,938 B2 | 8/2011 | Wang |
| 8,059,923 B2 | 11/2011 | Bates et al. |
| 8,108,030 B2 | 1/2012 | Castella et al. |
| 8,486,063 B2 | 7/2013 | Werneth et al. |
| 8,488,062 B2 | 7/2013 | Belhe et al. |
| 10,251,606 B2 * | 4/2019 | Matsubara ............... A61B 8/06 |
| 2002/0010487 A1 | 1/2002 | Evans et al. |
| 2004/0146546 A1 | 7/2004 | Gravett et al. |
| 2005/0196026 A1 | 9/2005 | Klingensmith et al. |
| 2005/0249391 A1 | 11/2005 | Kimmel et al. |
| 2006/0241342 A1 | 10/2006 | Macaulay et al. |
| 2007/0016034 A1 | 1/2007 | Donaldson |
| 2007/0232933 A1 | 10/2007 | Gille et al. |
| 2008/0119739 A1 | 5/2008 | Vardi et al. |
| 2008/0171944 A1 | 7/2008 | Brenneman et al. |
| 2008/0180683 A1 | 7/2008 | Kemp |
| 2008/0291463 A1 | 11/2008 | Milner et al. |
| 2009/0018393 A1 | 1/2009 | Dick et al. |
| 2009/0024085 A1 | 1/2009 | To et al. |
| 2009/0043191 A1 | 2/2009 | Castella et al. |
| 2009/0088650 A1 | 4/2009 | Corl |
| 2009/0195514 A1 | 8/2009 | Glynn et al. |
| 2009/0284332 A1 | 11/2009 | Moore et al. |
| 2010/0087732 A1 | 4/2010 | Eberle et al. |
| 2010/0130864 A1 | 5/2010 | Donnelly et al. |
| 2010/0220334 A1 | 9/2010 | Condit et al. |
| 2010/0256527 A1 | 10/2010 | Lippert |
| 2011/0060229 A1 | 3/2011 | Hulvershorn et al. |
| 2011/0152771 A1 | 6/2011 | Milner et al. |
| 2011/0306995 A1 | 12/2011 | Moberg |
| 2011/0319752 A1 | 12/2011 | Steinberg et al. |
| 2012/0108943 A1 | 5/2012 | Bates et al. |
| 2012/0230565 A1 | 9/2012 | Steinberg et al. |
| 2013/0030295 A1 | 1/2013 | Huennekens et al. |
| 2013/0030303 A1 | 1/2013 | Ahmed et al. |
| 2013/0046167 A1 | 2/2013 | Shah |
| 2013/0137980 A1 | 5/2013 | Waters et al. |

(56) References Cited

U.S. PATENT DOCUMENTS

| | | |
|---|---|---|
| 2013/0296704 A1 | 11/2013 | Magnin et al. |
| 2013/0303907 A1 | 11/2013 | Corl |

FOREIGN PATENT DOCUMENTS

| | | |
|---|---|---|
| EP | 1 820 436 A2 | 8/2007 |
| JP | 2009538644 A | 11/2009 |
| JP | 2017510312 A | 4/2017 |
| WO | 91/17710 A1 | 11/1991 |
| WO | 03/030744 A1 | 4/2003 |
| WO | 2013170207 A1 | 11/2013 |
| WO | 2014/100226 A1 | 6/2014 |
| WO | 2014/109879 A1 | 7/2014 |
| WO | 2014/143816 A1 | 9/2014 |
| WO | 2014/150401 A1 | 9/2014 |

OTHER PUBLICATIONS

Bail et al.; 'Optical coherence tomography with the "Spectral Radar" —Fast optical analysis in volume scatterers by short coherence interferometry' Optics letters vol. 21, No. 14 (1996) 1087-1089.

Ferring, et al., Vascular ultrasound for the pre-operative evaluation prior to arteriovenous fistula formation for haemodialysis: review of the evidence, Nephrol. Dial. Transplant. 23(6): 1809-1815, 2008.

Fleming et al., "Real-time monitoring of cardiac radio-frequency ablation lesion formation using an optical coherence tomography forward-imaging catheter. ," J. Biomed. Opt. 15, (3), 030516-030513 (2010).

Harrison et al., What's in a name?, J Endo Ther 14(6):797-801, 2011.

International Search Report and Written Opinion dated Apr. 10, 2015, for International Patent Application No. PCT/US2015/011397, filed Jan. 14, 2015 (14 pages).

International Search Report and Written Opinion dated Apr. 21, 2015, for International Patent Application No. PCT/US2015/011359, filed Jan. 14, 2015 (10 pages).

International Search Report and Written Opinion dated Apr. 28, 2015, for International Patent Application No. PCT/US2015/011357, filed Jan. 14, 2015 (11 pages).

International Search Report and Written Opinion dated Apr. 28, 2015, for International Patent Application No. PCT/US2015/011411, filed Jan. 14, 2015 (11 pages).

International Search Report and Written Opinion dated May 4, 2015, for International Patent Application No. PCT/US2015/011337, filed Jan. 14, 2015 (16 pages).

Kirkman, 1991, Technique for flow reduction in dialysis access fistulas, Surg Gyn Obstet 172(3):231-3.

Mickley, 2008, Steal Syndrome —strategies to preserve vascular access and extremity, Nephrol Dial Transplant 23:19-24.

Miller et al., 2006, Minimally Invasive Limited Ligation Endoluminal-assisted Revision (MILLER) for treatment of dialysis access-associated steal syndrome, Kidney Int 70(4):765-70.

Miller, et al., 2009, The MILLER banding procedure is an effective method for treating dialysis-associated steal syndrome, Kidney Int 1-8.

Rivers, et al., 1992, Correction of steal syndrome secondary to hemodialysis access fistulas: a simplified quantitative technique, Surgery 112(3):593-7.

Robbin, et al., Hemodialysis arteriovenous fistula maturity: US evaluation, Radiology 225(1):59-64, 2002.

Schneider, et al., 2006, T-banding: A technique for flow reduction of a hyper-functioning arteriovenous fistula, J Vasc Surg.

Seward et al, Mayo Clinic Proceedings 71(7):629-635 (1996).

Smith et al., 'Absolute displacement measurements using modulation of the spectrum of white light in a Michelson Interferometer' Applied Optics, vol. 28, No. 15. 1989. 3339-3342.

Toregeani et al., Evaluation of hemodialysis arteriovenous fistula maturation by color-flow Doppler ultrasound, J Vasc Bras 7(3)203-2013, 2008.

Wang et al. "In vivo intracardiac optical coherence tomography imaging through percutaneous access: toward image-guided radio-frequency ablation". J. Biomed. Opt. 0001;16(11):110505-110505-3. doi:10.1117/1.3656966.

Wang et al., "Optimizing the Beam Pattern of a Forward-Viewing Ring-Annular Ultrasound Array for Intravascular Imaging", Transactions on Ultrasonics, Ferroelectrics, and Frequency Control, vol. 49, No. 12, Dec. 2002.

West et al., Arterial insufficiency in hemodialysis access procedures: correction by banding technique, Transpl Proc 23 (2):1838-40, 1991.

\* cited by examiner

SYSTEMS AND METHODS FOR EVALUATING HEMODIALYSIS ARTERIOVENOUS FISTULA MATURATION

RELATED APPLICATIONS

The present application is a continuation of U.S. patent application Ser. No. 14/596,576 filed Jan. 14, 2015, which claims the benefit of and priority to U.S. provisional application Ser. No. 61/927,016, filed Jan. 14, 2014, the contents of which are incorporated by reference herein in their entireties.

FIELD OF THE INVENTION

The invention relates to evaluation of maturity of arteriovenous (AV) fistula using guidewires that measure intravascular blood flow and/or pressure.

BACKGROUND

Healthy kidneys remove waste and minerals from the blood. When kidneys fail, harmful waste builds up in the body, blood pressure may rise, and the body may retain excess fluid and not make enough red blood cells due to insufficient erythropoietin production. Hemodialysis is a common method for treating kidney failures and involves flowing blood through a filter to remove wastes. For hemodialysis, a fistula is created that connects an artery to a vein, or optionally an AV graft is created by using a tube to connect the artery to the vein. The National Kidney Foundation (NKF), Centers for Medicare and Medicaid Services (CMS), DaVita Patient Citizens (DPC) and other organizations and experts generally agree that fistulas are the best type of vascular access. After creation, a fistula can take several weeks to develop enough to be used, i.e., to reach fistula maturation. Hemodialysis can be unsuccessful or lead to complications if performed before, or too long after, fistula maturation. The evaluation of maturation by colorflow Doppler ultrasound has been proposed. See, e.g., Toregeani, et al., 2008, Evaluation of hemodialysis arteriovenous fistula maturation by color-flow Doppler ultrasound, J Vasc Bras 7(3):203-213 or Ferring, et al., 2008, Vascular ultrasound for the pre-operative evaluation prior to arteriovenous fistula formation for haemodialysis: review of the evidence, Nephrol. Dial. Transplant. 23(6):1809-1815.

Unfortunately, there are drawbacks associated with those procedures. For example, where the ultrasound catheter reveals that intravascular intervention is called for, the catheter must be swapped for a catheter that can perform the intervention (e.g., thrombectomy). Every removal and insertion of a new catheter raises risk of complications. Additionally, even though the ultrasound catheter itself provides some guidance to a treatment location, it does not provide direct navigational guidance for treatment after having been removed from the body. Further, even though medical organizations recommend fistula access, evaluating maturation is imperfect due to the fact that the ultrasound catheter being used to measure flow also partially impedes that flow. That is, the catheter itself partially occludes flow and interferes with obtaining an actual measurement of flow through an AV fistula.

SUMMARY

The invention provides methods of evaluating AV fistula maturation using an instrumented guidewire to measure intravascular blood flow and/or pressure. By using a small diameter guidewire that does not interfere substantially with the flow, an accurate measurement can be made that is useful for identifying when a fistula is mature and therefore ready to be used for hemodialysis. The guidewire can be instrumented to measure flow velocity, pressure, other properties, or a combination thereof. The guidewire can be operated with a system computer that uses the measurement to provide information that aids in evaluating maturity. Fistula maturation is correctly identified, allowing hemodialysis to be initiated at a suitable time, avoiding complications. This lowers cost of hemodialysis while improving results, leading to greater patient health. Additionally, since the quality of the fistula is evaluated by a guidewire, the same guidewire can be used to guide a catheter to a location proximal to where the measurement is made. Thus, where the guidewire detects or reveals a need for therapy, the guidewire can be used to guide delivery of the therapy via a catheter, without the need for a catheter exchange, thus decreasing complications associated with catheter exchanges.

In certain aspects, the invention provides a method for assessing maturation of a fistula that includes inserting an instrumented guidewire into a vessel of a patent. The vessel is in communication with a fistula, which provides fluid communication between the vessel and an adjacent vessel. For example, an arteriovenous fistula for hemodialysis may be assessed. The flow of blood through the fistula is measured using the guidewire and the measured flow of blood is used to determine if the fistula is mature. Measuring the flow of blood may include collecting data with a sensing device on the guidewire while the guidewire is within the vessel and relaying the data to a computer. The computer determines an observed rate of the flow of blood. Preferably a computer program is used to provide information about the maturity of the fistula based on the observed rate of blood flow. Determining maturation may be done by comparing the observed rate to a standard. For example, an observed rate of 600 mL/min or greater may indicate that the fistula is mature. The instrumented guidewire may include an ultrasonic transducer (e.g., for Doppler velocity), a pressure sensor, other sensors, or a combination thereof.

The guidewire may be specially designed for arteriovenous hemodialysis fistula. For example, the guidewire may be shorter than other intravascular guidewires, stiffer, or both. The guidewire may have a diameter of about 0.035 inches or less. In some embodiments, the guidewire is less than about 110 cm long, and preferably less than about 80 cm long (e.g., about 50 to 60 cm long). The guidewire can include a stiffening material to give it a desires flexural modulus (e.g., at least about 15 GPa, or at least about 50 GPa). In some embodiments, the guidewire will have a stiffness of 100 GPa flexural modulus or greater.

In certain embodiments, the method further includes sliding a catheter over the guidewire and using the catheter over the guidewire to deliver therapy to the fistula.

Aspects of the invention provide a system for assessing maturation of a fistula. The system includes a sensing guidewire comprising a sensor and configured to be inserted into a vessel of a patient and a computer communicatively linked with the sensing guidewire. The computer receives a measurement from the sensor and use the measurement to determine an observed rate of blood flow through a fistula. The system optionally can include a catheter to deliver therapy to the fistula. Preferably, the computer includes a program in memory that causes the computer to provide information about the maturity of the fistula based on the observed rate of blood flow.

DETAILED DESCRIPTION

Methods of the invention use a guidewire with one or more sensor to obtain intraluminal measurements within a body lumen. The sensors are preferably coupled to signal wires such as electrical conductors, which relay signals between the sensors and a workstation. A guidewire of the invention can include a pressure sensor, a flow sensor, a temperature sensor or combinations thereof. Preferably, the guidewire is a combination guidewire that includes both a pressure sensor and a flow sensor. Pressure sensors can be used to measure pressure within the lumen and flow sensors can be used to measure the velocity of blood flow. Temperature sensors can measure the temperature of a lumen. A guidewire with both a pressure sensor and a flow sensor provides a desirable environment in which to calculate fractional flow reserve (FFR) using pressure readings, and coronary flow reserve (CFR), or non-coronary vessel flow reserve, using flow readings.

Figure 1:
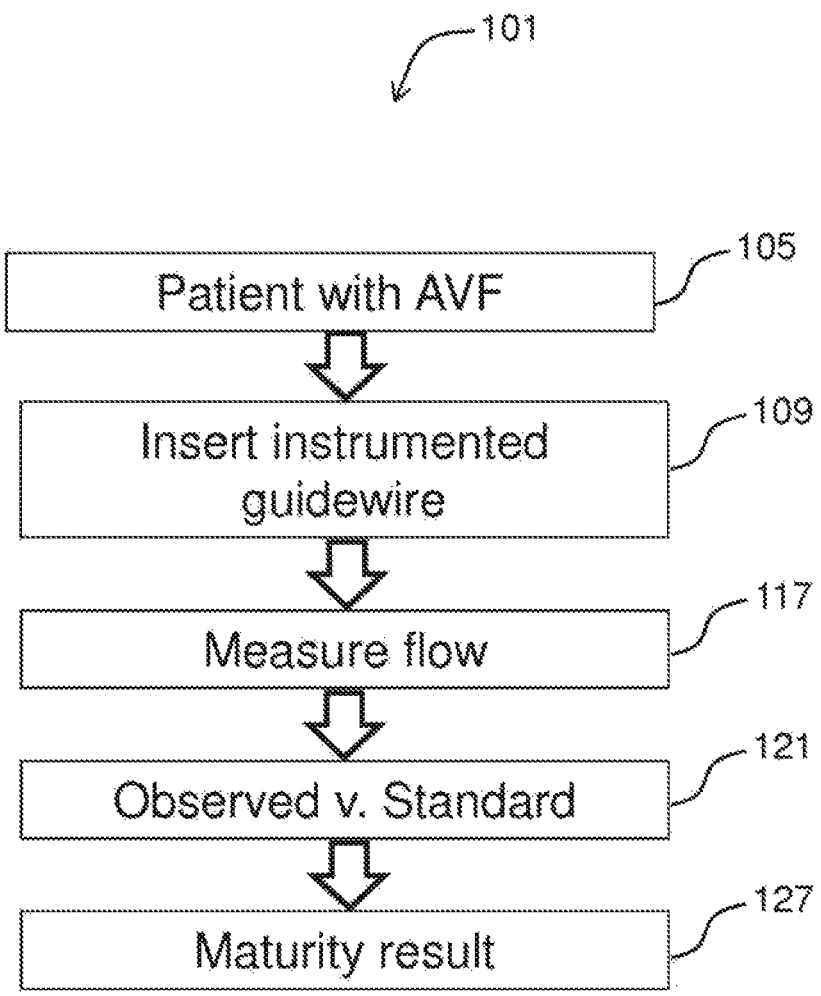
FIG. 1 diagrams a method of using a guidewire to assess fistula maturation.

FIG. 1 diagrams a method 101 of using a functional management wire (FM wire) to assess maturation of AV fistulas or grafts. Use of a wire results in less vessel obstruction than a catheter and offers the ability to intervene over the FM wire at the time of the procedure. An FM wire could provide flow measurements, pressure measurements, others, or a combination thereof.

Functional management is a guide wire based technology that analyzes pressure, flow, or both from the inside of a vessel. The wire provides a simple, reproducible measurement, and may be used in conjunction with angiography.

Method 101 starts 105 with a patient with an AV fistula. An instrumented guidewire is inserted 109 into the appropriate vessel to make measurements proximal (e.g., at or near) the AV fistula. In some embodiments, the guidewire is inserted 109 into the vein immediately downstream of the fistula. Preferably, measurements are made where flow is laminar. Measurements may be made following generally procedure described in Robbin, et al., 2002, Hemodialysis arteriovenous fistula maturity: US evaluation, Radiology 225(1):59-64. The flow of blood through the fistula or graft is measured 117.

The observed flow is blood is compared 121 to a standard (e.g., for a binary yes/no call, or to stratify). This can be done using a computer that receives data from the guidewire. The computer can further provide 127 a result supporting a determination of whether the fistula is mature. Any suitable instrumented guidewire can be used to measure 117 the blood flow. For example, a functional management guidewire can be used.

Figure 2:
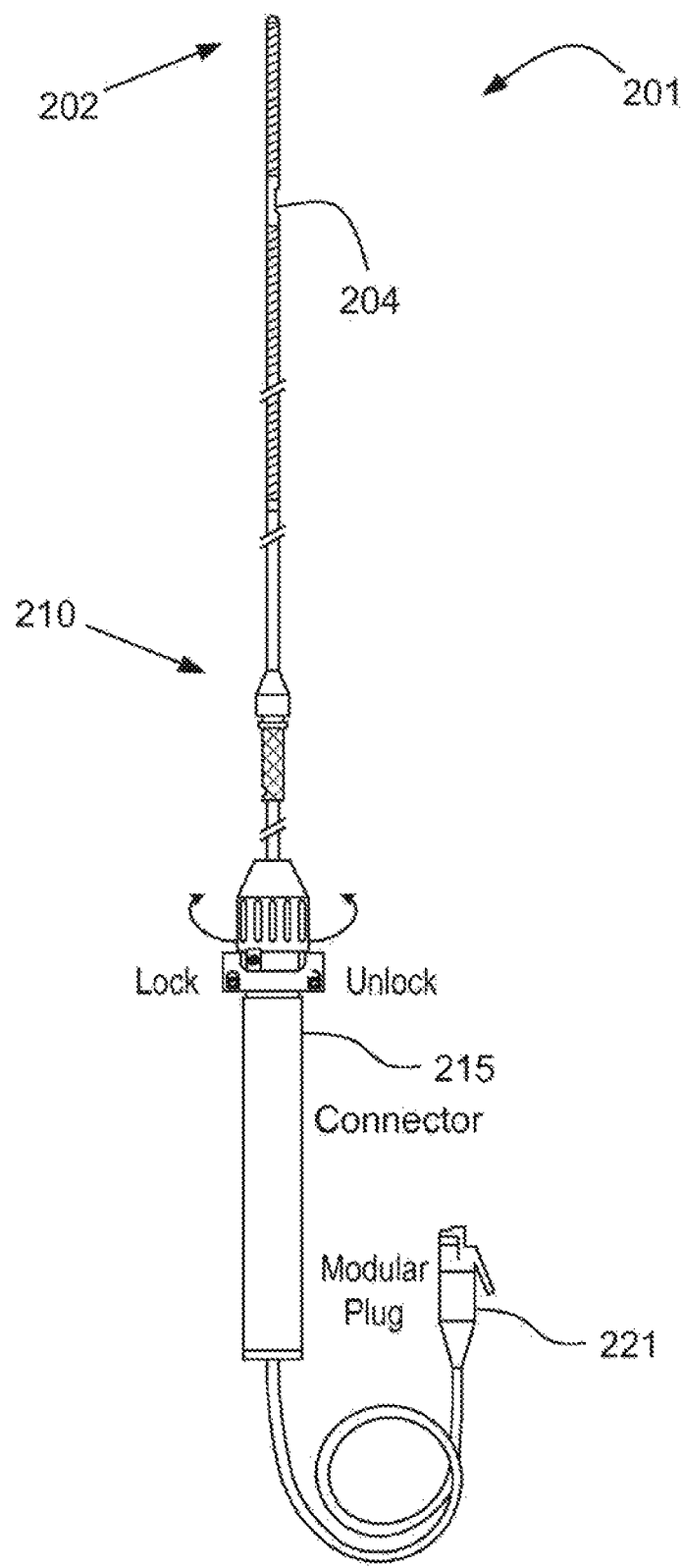
FIG. 2 illustrates a guidewire with a pressure sensor.

FIG. 2 illustrates a guidewire 201 with a pressure sensor 204. Guidewire 201 generally defines an elongated body extending from a proximal end 210 to a distal end 202. Proximal end 210 connects to connector housing 215, which offers a modular plug 221 for connection to a computing device in systems of the invention.

A pressure sensor allows one to obtain pressure measurements within a body lumen. A particular benefit of pressure sensors is that pressure sensors allow one to measure of fractional flow reserve (FFR) in vessel, which is a comparison of the pressure within a vessel at positions prior to the fistula and after the fistula. The level of FFR determines the patency of the fistula, which allows physicians to more accurately identify fistula maturation. For example, an FFR measurement above 0.80 may indicate maturation. Another benefit is that a physician can measure the pressure before and after an intraluminal intervention procedure to determine the impact of the procedure.

Pressure sensor 204 can be mounted on the distal portion of a flexible elongate member. In certain embodiments, the pressure sensor is positioned distal to the compressible and bendable coil segment of the elongate member. This allows the pressure sensor to move away from the longitudinal axis and coil segment as bended. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the flexible elongate member to the proximal portion of the flexible elongate member. Additional details of suitable pressure sensors that may be used with devices of the invention are described in U.S. Pat. No. 6,106,476. U.S. Pat. No. 6,106,476 also describes suitable methods for mounting the pressure sensor 404 within a sensor housing. As discussed above, additionally or alternatively, a guidewire can include a flow sensor. In some embodiments, a guidewire is used that includes a flow sensor. A suitable product for guidewire 201 is the PrimeWire PRESTIGE from Volcano Corporation.

In general, the guide wire of the present invention is comprised of a flexible elongate element having proximal and distal ends and a diameter of 0.018" and less as disclosed in U.S. Pat. Nos. 5,125,137, 5,163,445, 5,174,295, 5,178,159, 5,226,421, 5,240,437 and 6,106,476, all of which are incorporated by reference herein.

A guidewire of the invention may include a flexible elongate element having proximal and distal extremities, and can be formed of a suitable material such as stainless steel, Nitinol, polyimide, PEEK or other metallic or polymeric materials having an outside diameter for example of 0.018" or less and having a suitable wall thickness, such as, e.g., 0.001" to 0.002". This flexible elongate element is conventionally called a hypotube. In one embodiment, the hypotube may have a length of less than 120 cm, preferably about 50, 60, 70, or 80 cm. Typically, such a guide wire may further include a stainless steel core wire extending from the proximal extremity to the distal extremity of the flexible elongate element to provide the desired torsional properties to facilitate steering of the guide wire in the vessel and to provide strength to the guidewire and prevent kinking.

In a preferred embodiment, methods of the invention employ a guidewire with improved stiffness, relative to prior art guidewires. For example, the guidewire can include a stiffening material such as a stainless steel core or a less pliable plastic (e.g., less pliable than Nitinol, polyimide, or PEEK). Preferably, the guidewire has a flexural modulus of at least 15 GPa. In some embodiments, the guidewire has a flexural modulus of at least 50 GPa (e.g., as measured and described in Harrison et al., 2011, What's in a name?, J Endo Ther 18(6):797-801). For example, the guidewire may be made with the stiffness of an Amplatz type super-stiff or ultra-stiff guidewire. The guidewire can have a diameter of about 0.014" (0.35 mm) and can include the functional instrumentation of the Doppler guide wire sold under the name FLOWIRE by Volcano Corporation, the pressure guidewire sold under the name PRIMEWIRE PRESTIGE by Volcano Corporation, or both.

Figure 3:
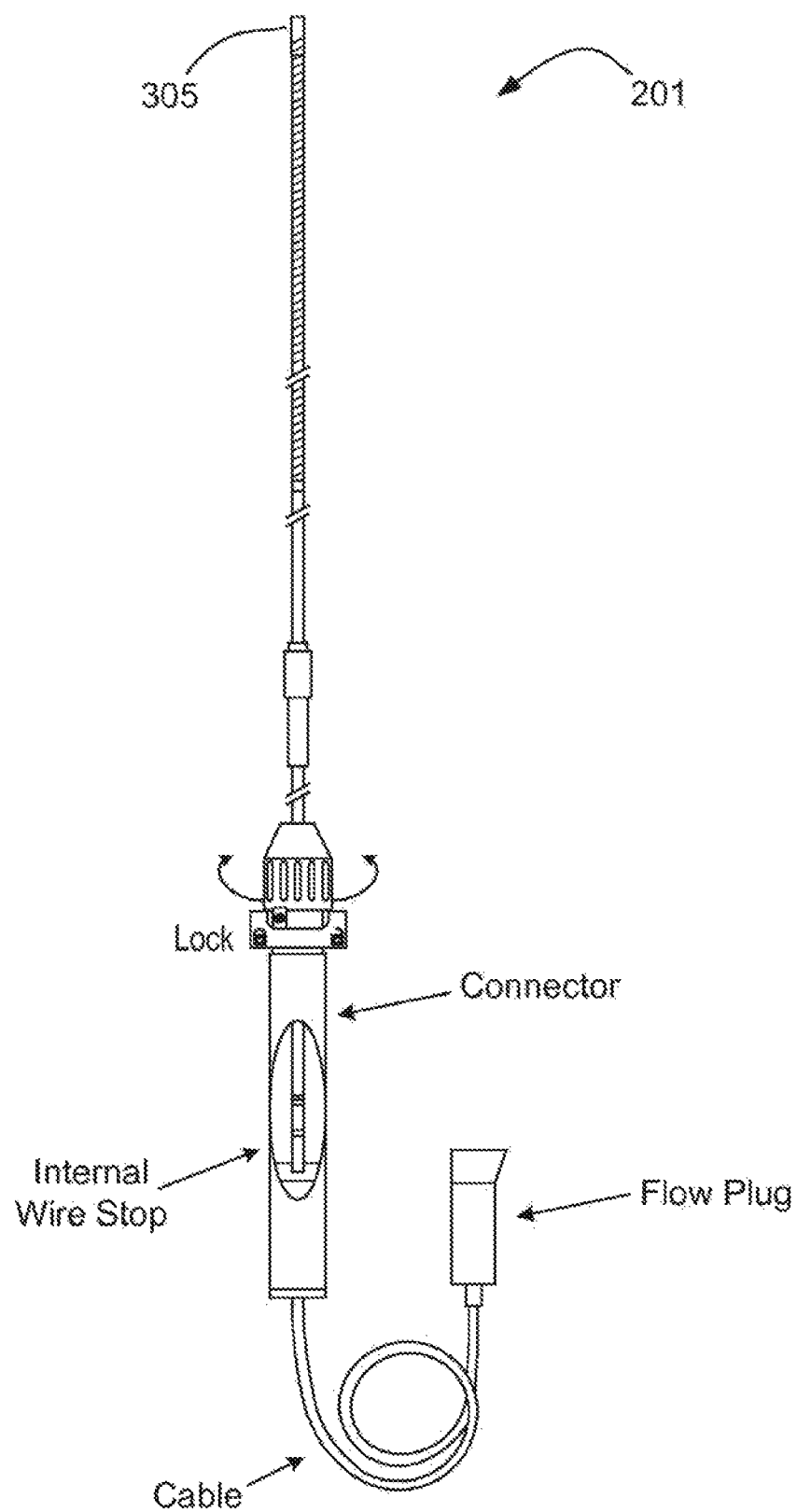
FIG. 3 illustrates a guidewire with a flow sensor.

FIG. 3 illustrates a guidewire 201 with a flow sensor 305. The flow sensor can be used to measure blood flow velocity within the vessel, which can be used to assess coronary flow reserve (CFR), or similar. The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835. A suitable product for guidewire 201 with a flow sensor 305 is the FLOWIRE from Volcano Corporation.

In a preferred embodiment, methods of the invention employ a guidewire that includes a device for measuring pressure and a device for measuring flow. For example, in use, the guidewire may be advanced to a fistula. The pressure and flow velocity may then be measured.

The ability to take the pressure and flow measurements at the same location and same time with the combination tip sensor, improves the accuracy of the diagnostic information.

Figure 4:
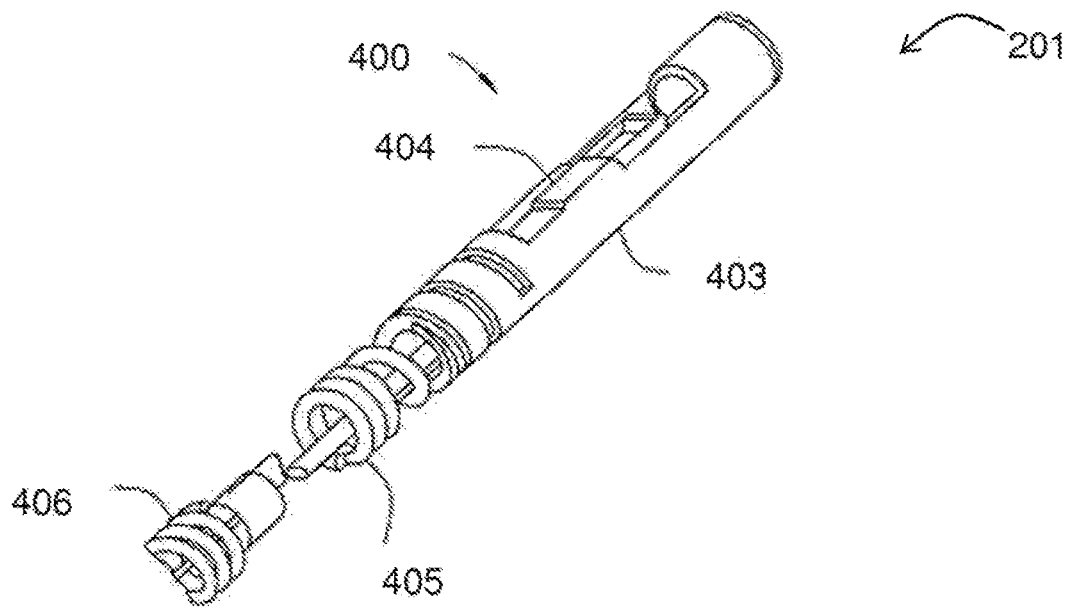
FIG. 4 shows a guidewire tip with a flow sensor and a pressure sensor.

FIG. 4 shows a combination sensor tip 400 of a guidewire 201 according to embodiments of the present invention. The combination sensor tip 400 includes a pressure sensor 404 within sensor housing 403, and optionally includes a radiopaque tip coil 405 distal to proximal coil 406.

Figure 5:
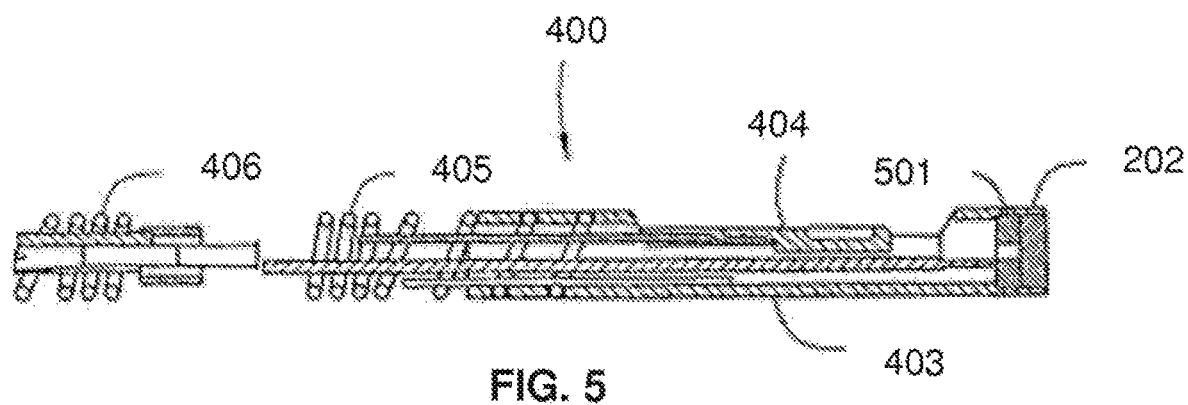
FIG. 5 gives a cross-sectional view through a guidewire tip.

FIG. 5 gives a cross-sectional view through combination sensor tip 400, showing ultrasound transducer 501 disposed therein. The ultrasound transducer 501 may be any suitable transducer, and may be mounted in the distal end using any conventional method, including the manner described in U.S. Pat. No. 5,125,137, which is fully incorporated herein by reference. Conductors (not shown) may be secured to the front and rear sides of the ultrasound transducer 501, and the conductors may extend interiorly to the proximal extremity of a guide wire.

The combination sensor tip 400 also includes a pressure sensor 404 also disposed at or in close proximity to the distal end 202 of the combination sensor tip 400. The pressure sensor 404 may be of the type described in U.S. Pat. No. 6,106,476, which is fully incorporated herein by reference. For example, the pressure sensor 404 may be comprised of a crystal semiconductor material having a recess therein and forming a diaphragm bordered by a rim. A reinforcing member may be bonded to the crystal to reinforce the rim of the crystal, and may have a cavity therein underlying the diaphragm and exposed to the diaphragm. A resistor having opposite ends may be carried by the crystal and may have a portion thereof overlying a portion of the diaphragm. Leads may be connected to opposite ends of the resistor and extend proximally within the guide wire. Additional details of suitable pressure sensors that may be used as the pressure sensor 404 are described in U.S. Pat. No. 6,106,476. U.S. Pat. No. 6,106,476 also describes suitable methods for mounting the pressure sensor 404 within the combination sensor tip 400. In one embodiment, the pressure sensor 404 is oriented in a cantilevered position within a sensor housing 403. For example, the sensor housing 403 preferably includes a lumen surrounded by housing walls. When in a cantilevered position, the pressure sensor 404 projects into the lumen of the sensor housing 403 without contacting the walls of the sensor housing 403.

In FIG. 5, ultrasound transducer 501 is illustrated as disposed near distal end 202. One advantage of the sensor housing 403 is that because the sensor housing 403 encloses both the ultrasound transducer 501 and the pressure sensor 404, the need for two separate housings, i.e., one for an ultrasound transducer and one for a pressure sensor, is eliminated. Accordingly, the use of a common sensor housing 403 for the ultrasound transducer 501 and the pressure sensor 404 makes the combination sensor tip 400 easier to manufacture than current designs.

Additionally, the combination sensor tip 400 of the present invention provides for both the ultrasound transducer 501 and the pressure sensor 404 to be disposed near the distal end of the combination sensor tip 400. The combination sensor tip 400 of the present invention is advantageous because by having both the ultrasound transducer 501 and the pressure sensor 404 near its distal end, the combination sensor tip 400 is capable of being positioned distally beyond the fistula. Additionally, the combination sensor tip 400 of the present invention, unlike the prior art, is also able to take measurements from the ultrasound transducer 501 and the pressure 104 at approximately the same location and approximately the same time, thereby resulting in greater consistency of measurements, greater accuracy of measurements, and greater accuracy of placement within the body. Furthermore, placement of both the ultrasound transducer 501 and the pressure sensor 404 near the distal end of the combination sensor tip 400 increases overall flexibility in a guide wire that incorporates the combination sensor tip 400. For example, a prior art guide wire that includes separate sensors, with the pressure sensor being located substantially proximal from the ultrasound transducer, has a longer relatively rigid area that must be devoted to the pressure and flow sensors, i.e., the distance from the ultrasound transducer to the pressure sensor. The present invention, in contrast, substantially reduces or entirely eliminates the distance between the ultrasound transducer and the pressure sensor, thereby allowing for increased flexibility across this length.

It should be noted that in an alternative embodiment of the combination sensor tip 400 (not shown) both the ultrasound transducer 501 and the pressure sensor 404 may be offset from the distal end of the combination sensor tip 400, such as, e.g., 1.5 cm to 3.0 cm from the distal end, but still located in close proximity to each other relative to prior art designs. Thus, the aforementioned advantages over the prior art design are still achieved.

In an alternative embodiment, the pressure sensor housing includes a tubular member having an opening on the outer wall in communication with the lumen and a tip. The tip is constructed of a solder ball. Alternatively, a weld, braze, epoxy or adhesive can be used. The lumen of the housing is counter-bored so that the lumen has a smaller inner diameter at the proximal end of the tubular member. For example, the housing may be constructed in the counter-bore fashion with a 0.010" inner diameter at the proximal end and a 0.012" inner diameter at the distal end, with the pressure transducer coaxially housed in the lumen. In addition, a flow sensor may be placed in the sensor tip instead of the weld, braze, epoxy or adhesive to provide a combo sensor tip. The advantage of the counter bore is that the housing is easier to make. The transducer is simply slid into place in the lumen and bonded (adhesive or epoxy) where the sides meet the proximal 0.010" inner diameter 314. The distal 0.012" inner diameter allows enough room for the pressure sensitive section of the transducer to be free from any contact with the housing. Because of the counter-bored lumen, there is no ledge that has to be made on the outer wall of the lumen, rather the pressure transducer communicates with the outside via an opening in the outer wall of lumen. Constructions suitable for use with a guidewire of the invention are discussed in U.S. Pub. 2013/0030303 to Ahmed, the contents of which are incorporated by reference.

A radiopaque tip coil 405 may be provided at the proximal end of the combination sensor tip 400. The radiopaque tip coil 405 is coupled to a proximal coil 106, and the proximal coil 106 may be coupled to the elongate tubular member. Another improvement of the present invention over current designs that use separate pressure sensor and ultrasound transducer housings is that the present invention provides a smoother transition from the elongate tubular member to the combination sensor tip 400, i.e., the connection between the radiopaque tip coil 405, the proximal coil 106, and the rest of the guide wire is optimized relative to current designs. Specifically, the transition is smoother and more flexible because of the absence of the housing between the radiopaque tip coil 405 and the proximal coil 106. Current designs generally have a tip coil 5 attached to a pressure sensor housing 3, which in turn is connected to a proximal coil 6. The present invention eliminates or greatly reduces the separation between the tip coil and the proximal coil that is required in current devices. Suitable coils for use with the present invention are described in U.S. Pat. No. 6,106,476.

Figure 6:
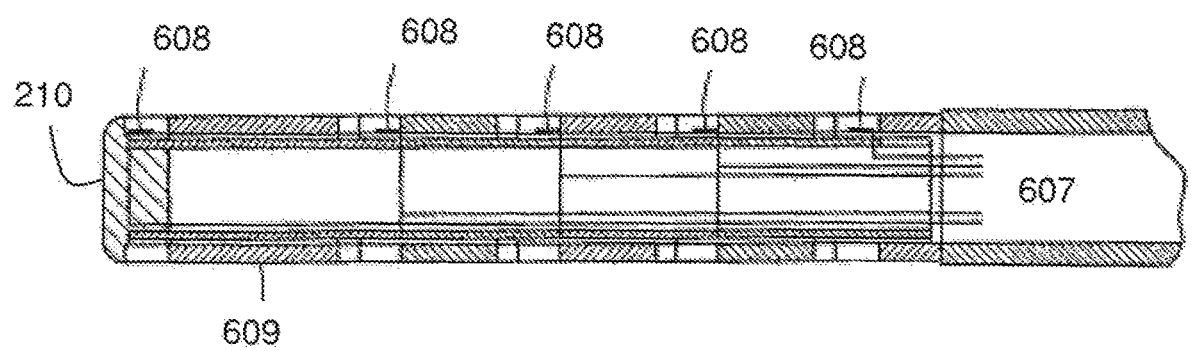
FIG. 6 shows conductors passing through a guide wire.

FIG. 6 shows fine wire conductors 607 passing through the guide wire to conductive bands 608 near the proximal end 210 of the guide wire. Signals from the ultrasound transducer 501 and the pressure sensor 404 may be carried by conductors 607. Usually three electrical connectors are necessary for a stand-alone pressure measurement guidewire and two electrical connectors are necessary for a stand-alone flow measurement guidewire. Thus, a guide wire incorporating the combination sensor tip 400 of the present invention includes five electrical conductors 607 extending through the lumen of the guidewire and five conductive bands 608 on the proximal end 610 of the guidewire. The conductive bands 608 may be electrically isolated from each other by means of epoxy 609. Alternatively, polyimide tubes may be used to isolate conductors from the conductive bands.

The electrical connection wires can include a conductive core made from a conductive material, such as copper, and an insulating coating, such as a polyimide, Fluoro-polymer, or other insulating material. The electrical connection wires extend from one or more sensors located on the distal end of the guidewire, run down the length of the guidewire, and connect to a connector housing at a proximal end.

Any suitable arrangement of the electrical connection wires through the length of the elongate member can be used. The arrangement of electrical connection wires must provide for a stable connection from the proximal end of the guidewire to the distal end of the guidewires. In addition, the electrical connection wires must be flexible and/or have enough slack to bend and/or move with the adjustable distal portion without disrupting the sensor connection. In one embodiment, the electrical connections run next the core member within the lumen of the elongate member.

In yet another embodiment, the electrical connector wires 707 are wrapped around a core member of the guidewire and then covered with a polyimide layer. At a distal end of the core member near the sensors, the polyimide layer can be dissected away, which frees the wires to extend and connect to their respective sensors. The length of the electrical connector wire running free from the core member and connected to the sensor should have enough slack/flexibility to remain connected to the sensor during bending of the guidewire.

Preferably, proximal end 610 connects to connector housing 215 as shown in FIG. 2. In certain embodiments, the electrical connector wires are joined together to form a male connector at a proximal end. The male connector mates with a female connector of the connector housing. The termination of the male connector can be performed by a metal deposition process as described in U.S. Pat. No. 6,210,339, incorporated herein by reference in its entirety. The deposited metal (or any conductive material) permanently adheres or couples to the exposed conductive wires at points where the polyimide layers were removed. After the masking material is removed, there are independent conductive stripes, each connected to a different respective electric wire. Because of the precision nature of the winding process as well as the masking and metal deposition processes, a male connector is made that is short in length, yet very reliable, in mating with a female connector and cable. Alternatively, conductive bands may be coupled to the exposed ends of the electric wires instead of the metallizing process.

The connector housing can be connected to an instrument, such as a computing device (e.g. a laptop, desktop, or tablet computer) or a physiology monitor that converts the signals received by the sensors into pressure and velocity readings in systems of the invention.

In advanced embodiments, the systems of the invention incorporate focused acoustic computed tomography (FACT), which is described in WO2014/109879, incorporated herein by reference in its entirety.

Figure 7:
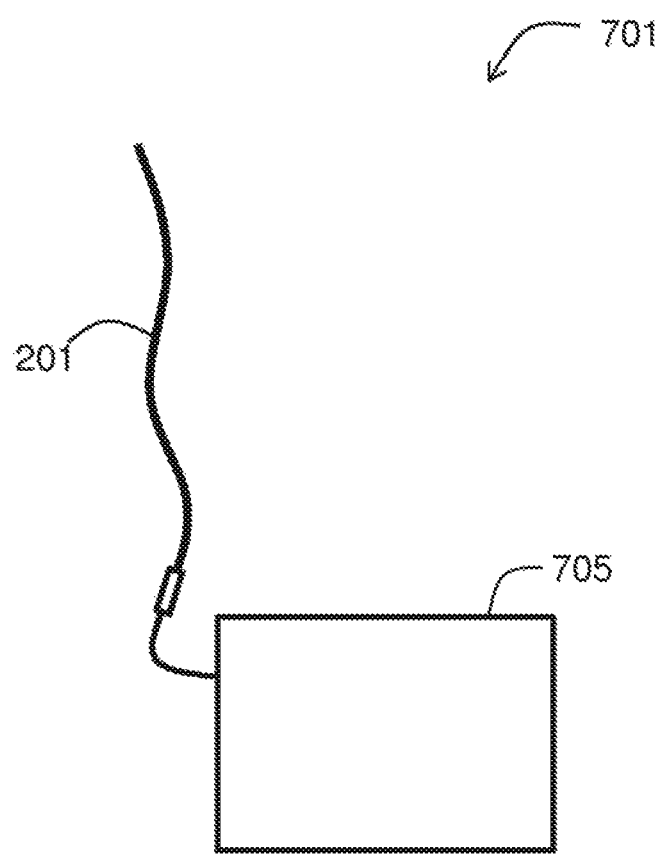
FIG. 7 illustrates a system of the invention.

FIG. 7 illustrates a system 701 of the invention. System 701 includes an instrumented guidewire 201 operably coupled to a computer device 705. Guidewire 201 includes at least one sensor such as a pressure sensor or flow sensor as discussed above. Guidewire 201 may include a plurality of sensor such as a pressure sensor and a flow sensor as discussed above. Computer 705 can be a dedicated medical imaging instrument, a standard desktop, laptop, or tablet computer, or a combination thereof (e.g., a medical imaging instrument with a base station and a laptop or desktop computer attached to provide a workstation and interface for a physician. Computer 705 can receive a measurement from the sensor on guidewire 201 and use the measurement to determine an observed rate of blood flow through a fistula. In some embodiments, computer 705 compares the observed rate of a blood flow to a standard or an expected rate of blood flow to provide an aid in assessing fistula maturation. For example, computer 705 may have a software program in memory that stores a standard (e.g., 600 mL/min) flow rate. By making a comparison, if a flow rate is sub-standard, the fistula can be deemed to be not mature. If the flow rate meets the standard, the fistula may be deemed mature. The instrument can further calculate Coronary Flow Reserve (CFR)—or similar—and Fractional Flow Reserve (FFR) and provide the readings and calculations to a user via a user interface.

In some embodiments, a user interacts with a visual interface to view images from the imaging system. Input from a user (e.g., parameters or a selection) are received by a computer device or processing instrument. Electrical signals are relayed from the conductors via a mating connector (or contact housing as described herein with respect to a connector of the present invention) to an instrument, such as, e.g., a physiology monitor, that converts the signals into pressure and velocity readings that are displayed to the user. In addition, algorithms such as Coronary Flow Reserve (CFR)—or similar—and Fractional Flow Reserve (FFR) are calculated.

System 701 may include one or a plurality of computer. For example, system 701 may include computer 705 as a bed-side workstation or in a control room and system 701 may additionally include a server computer for processing measurements or for receiving measurements from a plurality of Cath labs. A computer in system 701 such as computer 705 generally includes a processor coupled to memory and one or more input/output devices. Computer 705 may be provided by a desktop computer, laptop, tablet, mobile device, or purpose-built machine (such as a bed-side control station for a medical imaging system).

A processor generally refers to a computer microchip such as the processor sold under the trademark CORE 17 by Intel (Santa Clara, Calif.).

Memory generally includes one or more devices for random access, storage, or both. Preferably, memory includes a tangible, non-transitory computer readable medium, and may be provided by one or more of a solid state drive (SSD), a magnetic disc drive (aka, "a hard drive"), flash memory, an optical drive, others, or a combination thereof.

An I/O device may include one or more of a monitor, keyboard, mouse, touchscreen, Wi-Fi card, cell antenna, Ethernet port, USB port, light, accelerometer, speaker, microphone, drive for removable disc, others, or a combination thereof. Preferably, any combination of computer in system 701 may communicate through the use of a network, which may include communication devices for internet communication, telephonic communication, others, or a combination thereof.

As will be appreciated from the above, the invention provides systems and methods for evaluating the maturation of arteriovenous (AV) fistula using an instrumented guidewire that measures intravascular flow and/or pressure (an FM wire). By using a small diameter guidewire that does not interfere substantially with the flow, an accurate measurement can be made that is useful for identifying when a fistula is mature and therefore ready to be used for hemodialysis. The flow of blood through the fistula is measured using the guidewire and the measured flow of blood is used to determine if the fistula is mature. Preferably, the guidewire has a flexural modulus of at least 15 GPa and preferably at least 50 GPa. The guidewire may be made with the stiffness of an Amplatz type super-stiff or ultra-stiff guidewire. The guidewire can have a diameter of about 0.014" (0.35 mm) to 0.035" (0.89 mm). The guidewire may have length of less than 120 cm (e.g., about 80 cm). The guidewires may be provided in a system that includes a computer (that includes a processor coupled to a tangible, non-transitory memory) that analyzes flow measurements to evaluate fistula maturation (e.g., comparing the measured flow to a standard). The standard may be 600 mL/min and the computer can aid the determination that flow that meets or exceeds the standard indicates fistula maturation.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A tangible, non-transient computer readable medium comprising microprocessor executable instructions that, when executed, perform operations comprising:
   receiving, from a flow sensor, a first flow rate measurement of blood through a fistula in fluid communication with a vessel;
   receiving, from a pressure sensor, a first pressure measurement of blood adjacent the fistula;
   determining, using the first flow rate measurement and the first pressure measurement, whether a therapy to the fistula is indicated;
   providing a result indicative of a need to apply therapy to the fistula;
   after determining whether the therapy to the fistula is indicated, receiving a second flow rate measurement of blood through the fistula and a second pressure measurement of blood adjacent the fistula; and
   determining, using the second flow rate measurement and the second pressure measurement, whether further therapy to the fistula is indicated.

2. The tangible, non-transient computer readable medium of claim 1, wherein the microprocessor executable instructions for determining, using the first flow rate measurement and the first pressure measurement, whether a therapy to the fistula is indicated comprises comparing the first flow rate measurement to a predetermined flow rate.

3. The tangible, non-transient computer readable medium of claim 2, whereupon the first flow rate measurement equal to or greater than the predetermined flow rate, the therapy is indicated.

4. The tangible, non-transient computer readable medium of claim 3, wherein the predetermined flow rate is 600 mL/min.

5. The tangible, non-transient computer readable medium of claim 1, wherein the microprocessor executable instructions for determining, using the first flow rate measurement and the first pressure measurement, whether a therapy to the fistula is indicated comprises determining whether the fistula is mature.

6. The tangible, non-transient computer readable medium of claim 1, wherein the microprocessor executable instructions for determining, using the first flow rate measurement and the first pressure measurement, whether a therapy to the fistula is indicated comprises determining a level of maturation of the fistula.

7. The tangible, non-transient computer readable medium of claim 6, wherein determining the level of maturation of the fistula is based upon whether the first flow rate measurement is equal to or greater than a predetermined flow rate.

8. The tangible, non-transient computer readable medium of claim 7, wherein the predetermined flow rate of blood is 600 mL/min.

9. The tangible, non-transient computer readable medium of claim 6, wherein determining the level of maturation of the fistula is based upon whether the first pressure measurement is greater than a predetermined pressure.

10. The tangible, non-transient computer readable medium of claim 9, wherein the first pressure measurement is indicative of a fractional flow reserve.

11. The tangible, non-transient computer readable medium of claim 10, wherein the predetermined pressure is 0.80.

12. The tangible, non-transient computer readable medium of claim 7, wherein determining a level of maturation of the fistula is based upon whether the first pressure measurement is greater than a predetermined pressure.

13. The tangible, non-transient computer readable medium of claim 12, wherein the first pressure measurement is indicative of a fractional flow reserve.

14. The tangible, non-transient computer readable medium of claim 13, wherein the predetermined pressure is 0.80.

15. The tangible, non-transient computer readable medium of claim 1, wherein the microprocessor executable instructions for determining, using the first flow rate measurement and the first pressure measurement, whether a therapy to the fistula is indicated comprises comparing the first pressure measurement to a predetermined pressure.

16. The tangible, non-transient computer readable medium of claim 15, whereupon the first pressure measurement being greater than the predetermined pressure, the therapy is indicated.

17. The tangible, non-transient computer readable medium of claim 16, wherein the predetermined pressure is 0.80.

18. A system for assessing a fistula, the system comprising:
   a guidewire comprising a flow sensor and a pressure sensor; and
   a computer communicatively coupled to the guidewire, wherein the computer comprises a memory and executable instructions stored in the memory, whereupon being executed, the executable instructions perform operations comprising:
      receiving, from the flow sensor, a first flow rate measurement of blood through a fistula in fluid communication with a vessel;
      receiving, from the pressure sensor, a first pressure measurement of blood adjacent the fistula;
      determining, using the first flow rate measurement and the first pressure measurement, whether a therapy to the fistula is indicated;
      providing a result indicative of a need to apply therapy to the fistula;
      receiving a second flow rate measurement of blood through the fistula and a second pressure measurement of blood adjacent the fistula; and
      determining, using the second flow rate measurement and the second pressure measurement, whether further therapy to the fistula is indicated.

19. The system of claim 18, wherein the microprocessor executable instructions for determining, using the first flow rate measurement and the first pressure measurement, whether the therapy to the fistula is indicated comprises comparing the first flow rate measurement to a predetermined flow rate and comparing the first pressure measurement to a predetermined pressure.

20. The system of claim 19, whereupon the first flow rate measurement being equal to or greater than the predetermined flow rate and the first pressure measurement being equal greater than the predetermined pressure, the therapy is indicated.

* * * * *